United States Patent [19]
Shim et al.

[11] Patent Number: 5,647,974
[45] Date of Patent: Jul. 15, 1997

[54] HEXAGONAL MOLECULAR STRUCTURE WATER MANUFACTURING APPARATUS AND A METHOD THEREOF

[75] Inventors: Jin Hak Shim, Busan; Jun Il Song, Kyungsangnam-Do, both of Rep. of Korea

[73] Assignee: Goldstar Co., Ltd., Seoul, Rep. of Korea

[21] Appl. No.: 366,972

[22] Filed: Dec. 30, 1994

[30] Foreign Application Priority Data

Jul. 15, 1994 [KR] Rep. of Korea ............... 17121/1994
Oct. 27, 1994 [KR] Rep. of Korea ............... 27646/1994

[51] Int. Cl.$^6$ ..................................... C02F 1/48
[52] U.S. Cl. .................. 210/103; 210/138; 210/143; 210/222
[58] Field of Search .................... 210/103, 222, 210/138, 143; 366/141, 142, 144, 145, 273, 274

[56] References Cited

U.S. PATENT DOCUMENTS 4,725,149  2/1988  Kawakami et al. ............ 366/141

FOREIGN PATENT DOCUMENTS 2597468  10/1987  France ......................... 210/222
3322409   1/1985  Germany ....................... 366/274
3520361  12/1986  Germany ....................... 366/273

Primary Examiner—Matthew O. Savage
Attorney, Agent, or Firm—Fliesler, Dubb, Meyer & Lovejoy

[57] ABSTRACT

An improved hexagonal molecular structure water manufacturing apparatus and a method thereof capable of manufacturing hexagonal molecular structure water by rotating a permanent magnet in a hexagonal molecular structure water container of a refrigerator, which include a weight detection section for detecting the weight of water corresponding to a load of alternating water; a motor driving section for driving the motor in accordance with the detected weight; and a microcomputer for controlling the weight detection section and the motor driving section, respectively, and include a first step which detects whether or not the temperature of water is within a predetermined range; a second step which detects the amount of water when the temperature of the water of the first step is within a predetermined range; and a third step which drives a motor, alternating water in accordance with the detected weight of the second step, for a predetermined time.

5 Claims, 7 Drawing Sheets

HEXAGONAL MOLECULAR STRUCTURE WATER MANUFACTURING APPARATUS AND A METHOD THEREOF

BACKGROUND OF THE INVENTION

1. Field of the Invention

The present invention relates to a hexagonal molecular structure water manufacturing apparatus and a method thereof, and particularly to an improved hexagonal molecular structure water manufacturing apparatus and a method thereof capable of advantageously detecting the temperature inside a refrigerating chamber of a refrigerator and weighing water in a hexagonal molecular structure water container, thereby accurately controlling the operating time of a motor in accordance with a detected signal and rotating a rotatably alternating permanent magnet in the hexagonal molecular structure water container, so that pure water or common water, i.e., piped water, can be easily converted into hexagonal molecular structure water.

2. Description of the Conventional Art

Conventionally, hexagonal molecular structure water is well known for keeping the human body healthy because it has some elements helpful for cell activation, and as a result hexagonal molecular structure water is helpful in preventing various kinds of diseases such as cancer, constipation, diabetes and gastroenteric disorder.

Meanwhile, a commonly used conventional water polarity alternating apparatus, referring to FIG. 1, includes a motor 1 disposed at the bottom portion inside a body 3 thereof, a rotary magnet 2 connected to an upper end of a shaft of the motor 1, a container 4 disposed above the body 3 for receiving water therein, and a magnet 5 disposed at a predetermined portion in the container 4 for alternating the polarity of water in the container 4.

The detailed operation of the conventional alternating apparatus will now be explained.

To begin with, in the state that any type of liquid, i.e., water, is filled in the container 4, and when power is applied to the motor 1, the magnet 2 drivingly connected to the shaft of the motor 1 rotates. At this time, the magnet 5 rotates thereby and then a flow of water is created in the container 4.

However, the conventional alternating apparatus has drawbacks in detecting a stream load of water and a temperature thereof which need to be determined for manufacturing hexagonal molecular structure water.

SUMMARY OF THE INVENTION

Accordingly, it is an object of the present invention to provide a hexagonal molecular structure water manufacturing apparatus and a method thereof.

It is another object of the present invention to provide an improved hexagonal molecular structure water manufacturing apparatus and a method thereof capable of manufacturing hexagonal molecular structure water by rotating a permanent magnet in a hexagonal molecular structure water container of a refrigerator.

To achieve the object, there is provided a hexagonal molecular structure water manufacturing apparatus which includes a weight detection section for detecting the weight of water in the container; a motor driving section for driving the motor in accordance with the detected weight; and a microcomputer for controlling the weight detection section and the motor driving section, respectively.

To achieve the object, there is provided a hexagonal molecular structure water manufacturing method which includes a first step which detects whether or not the temperature of water is within a predetermined range; a second step which detects amount of water when the temperature of the water of the first step is within a predetermined range of temperature; and a third step which drives a motor, alternating water in accordance with the detected weight of the second step, for a predetermined time.

DETAILED DESCRIPTION OF THE INVENTION

Figure 1:
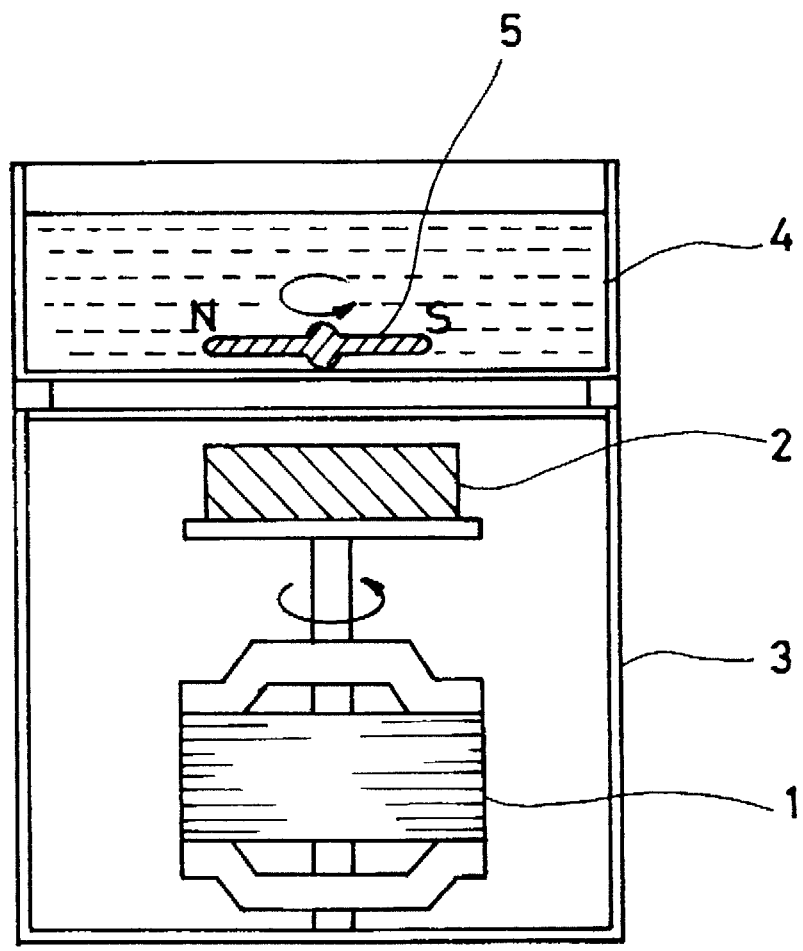
FIG. 1 is a schematic cross-sectional view showing a conventional alternating apparatus.
Figure 2:
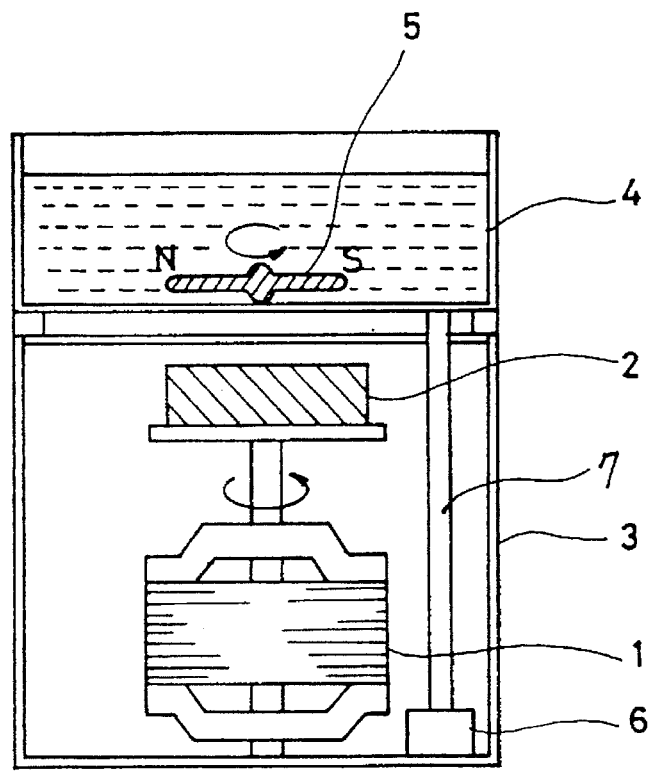
FIG. 2 is a schematic cross-sectional view showing a hexagonal molecular structure water manufacturing apparatus of a first embodiment according to the present invention.

Referring to FIG. 2, a hexagonal molecular structure water manufacturing apparatus of a first embodiment according to the present invention includes a weight detection sensor 6 disposed at a predetermined bottom portion of a refrigerating chamber of a refrigerator, a weight support shaft 7 disposed between the weight detection sensor 6 and a container 4, a circuit section(not shown) for controlling the weight detection sensor 6. The remaining elements are the same as in FIG. 1.

Figure 4:
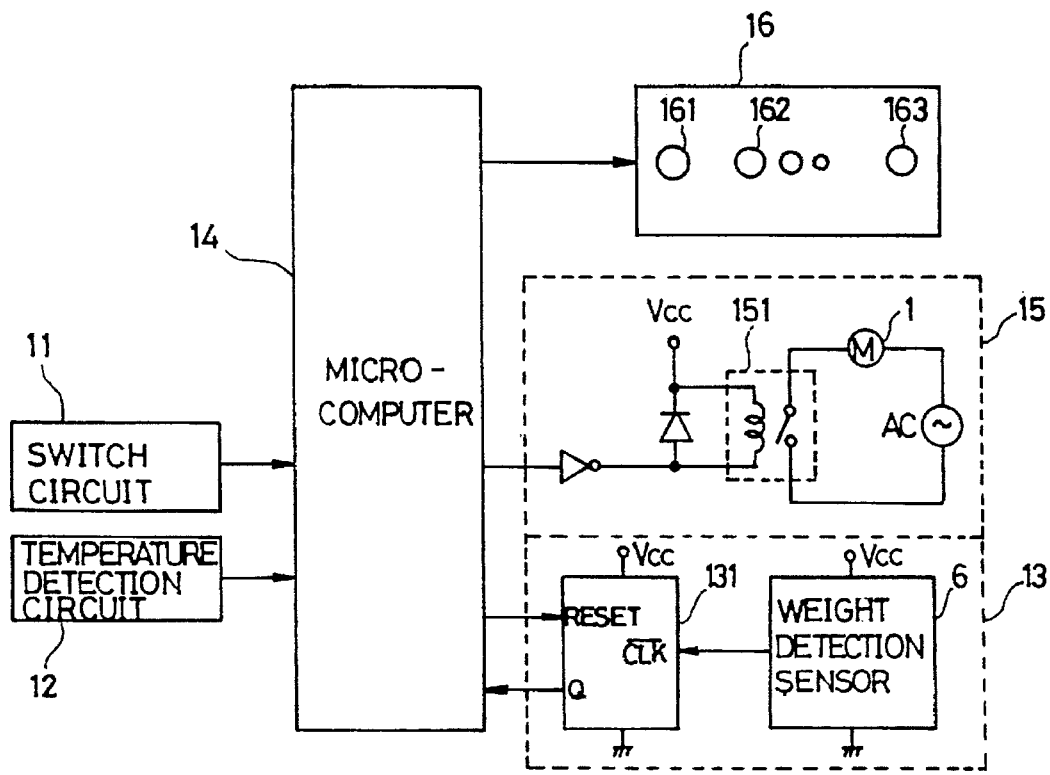
FIG. 4 is a block diagram showing a control circuit of the hexagonal molecular structure water manufacturing apparatus shown in FIG. 2 of the present invention.

Referring to FIG. 4, a control circuit adapted in the hexagonal molecular structure water apparatus according to the present invention includes a switch detection circuit 11 for detecting a state of a switch, a temperature detection circuit 12 for detecting the temperature in a refrigerating chamber of a refrigerator, a weight detection circuit 13 for weighing the amount of water in the container 4 and for generating a predetermined frequency in accordance with the detected weight, a microcomputer 14 for computing the weight based on the output of the weight detection circuit and for outputting a control signal in accordance with the computed weight, a motor driving circuit 15 for supplying electric power(AC) to the motor 1 in accordance with the control sisal outputted from the microcomputer 14, and a display circuit 16 for displaying a hexagonal molecular structure water manufacturing state in accordance with the control signals of the microcomputer 14.

Figure 5:
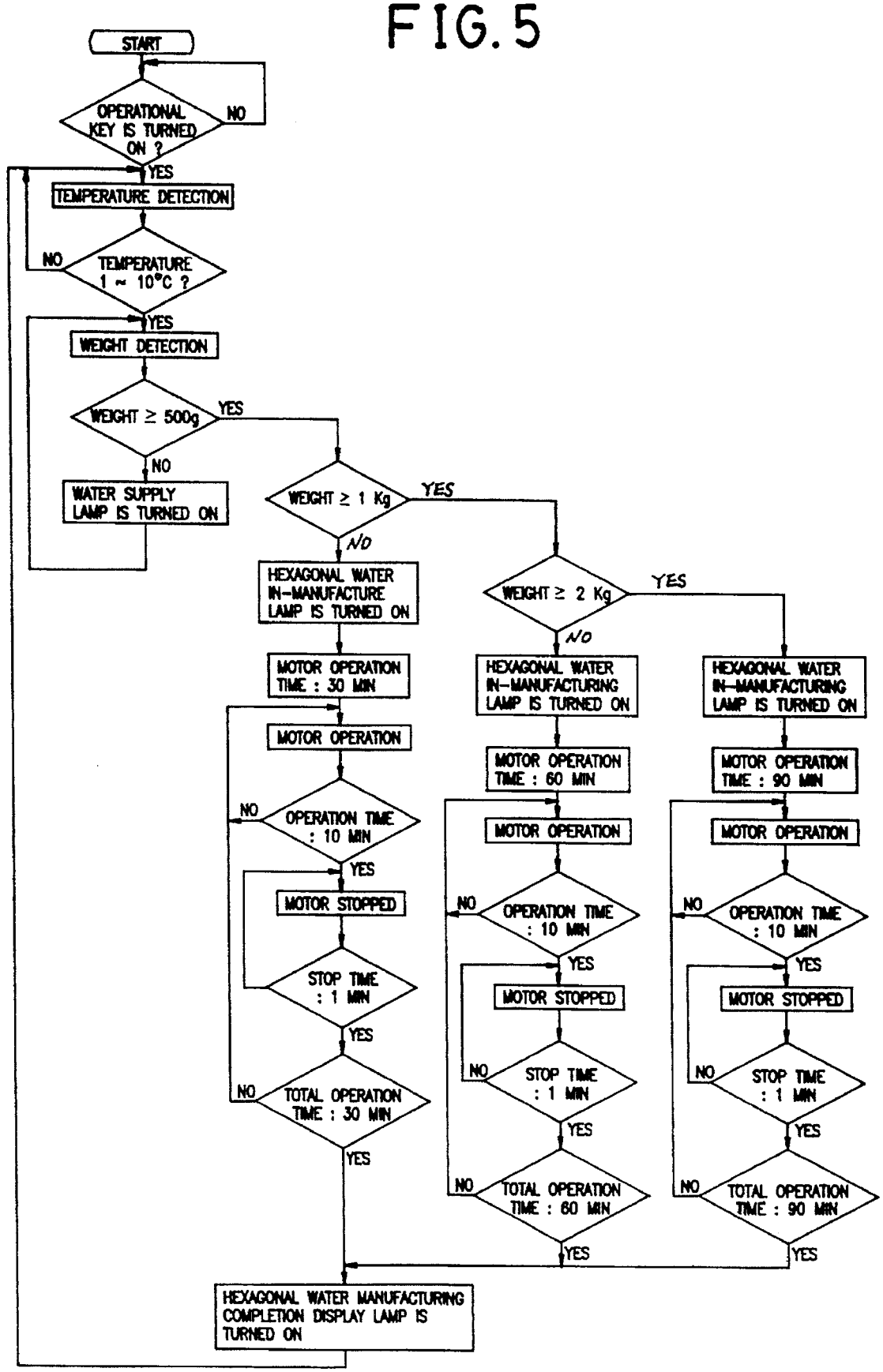
FIG. 5 is a flow chart showing a hexagonal molecular water manufacturing method shown in FIG. 4.

The detailed operation and effects thereof will now be explained with reference to FIGS. 3 to 5.

To begin with, in the state that the container 4 is substantially filled with water, when a user turns on an operating key(not shown) of the switch circuit 11 to begin the manufacturing of hexagonal molecular structure water, the microcomputer 14 detects the turned-on state and inputs data corresponding to the temperature in a refrigerating chamber which is detected by a temperature sensor(not shown). Thereafter, the microcomputer 14 judges whether or not the temperature is within a range between 1° C. and 10° C. If the temperature is not within the range, the operation of the microcomputer 14 returns back to a predetermined operation to detect the temperature. If the temperature is within the range, the microcomputer 14 outputs a frequency corresponding to the weight of water in the container 4.

Figure 3:
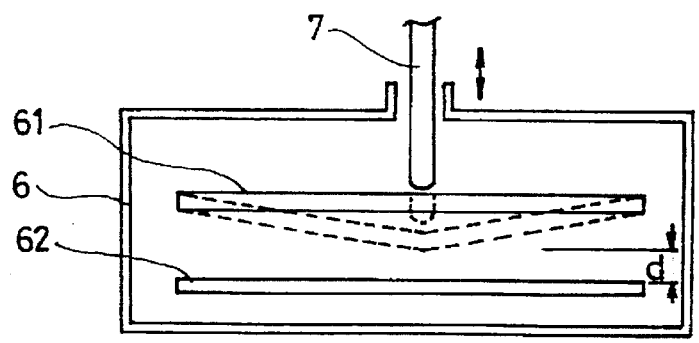
FIG. 3 is a view showing an operation of a weight detection sensor of the hexagonal molecular structure water manufacturing apparatus shown in FIG. 2 of the present invention.

That is, referring to FIGS. 2 and 3, as a weight support shaft 7 moves downwardly in accordance with the weight of water in the container 4, an upper electrode 61 of the weight detection sensor 6 moves downwardly toward a lower electrode 62.

Accordingly, the distance between the upper and lower electrodes 61 and 62 decreases and thus the capacitance C of the weight detection sensor 6 increases by the following formula.

$$C = \epsilon_0 \epsilon_R \frac{s}{d}$$

where S is the surface of an electrode, and $\epsilon_0 \epsilon_R$ is a dielectric ratio.

In addition, the oscillating frequency outputted from the weight detection sensor 6 is given by $$f \alpha \frac{1}{R \times C}$$

where R is the resistance of a weight detection sensor.

Finally, when the weight increases, the weight detection sensor 6 outputs a low oscillating frequency, and on the contrary when the weight decreases, a high oscillating frequency is outputted.

In addition, the counter IC 131 counts the frequency inputted to a clock terminal CLK and transfers the counted value to the microcomputer 14.

Thereafter, the microcomputer 14 inputs the counted value of the weight detection circuit 13. If the detected weight corresponding to the counted value is not over 500 g, the operation returns back to the weight detection step after turning on the water supply indicating lamp 161 of the display detection circuit 16. If the detected weight corresponding to the counted value is over 500 g, the microcomputer 14 judges whether or not the detected weight is over 1000 g.

When the detected weight is not over 1000 g, the microcomputer 14 turns on the lamp 162 which indicates that hexagonal molecular structure water is being manufactured and turns on the relay 151 of the motor driving circuit 151 after setting an operation time at 30 minutes, so that the motor 1 operates for 10 minutes and stops for 1 minute.

Thereafter, as the motor 1 rotates, the magnet 2 connected to the shaft thereof rotates, so that a flow of water is created in the container 4 and then hexagonal molecular structure water is manufactured therein.

When the total operation time of 30 minutes has lapsed, the microcomputer turns on the lamp 163 which indicates that the manufacture of the hexagonal molecular structure water is completed.

Meanwhile, the microcomputer 14 judges whether or not the detected weight is within 2000 g when the detected weight is over 1000 g. At this time, the microcomputer 14 turns on the lamp 162 which indicates that the manufacture of the hexagonal molecular structure water is being manufactured and turns on the relay 151 after setting an operation time at 60 minutes, so that the motor 1 works for 10 minutes and stops for 1 minute.

Thereafter, when the total operation time of 60 minutes is finished, the microcomputer 14 turns on the lamp 163 which indicates the completion of the manufacture of the hexagonal molecular structure water.

In addition, the microcomputer 14 turns on the lamp 162 which indicates that the hexagonal molecular structure water is being manufactured when the detected weight is over 2000 g and sets the operation time at 90 minutes, so that the motor 1 operates for 10 minutes and stops for 1 minute.

When the total operation time of 90 minutes has lapsed, the microcomputer 14 turns on the lamp 163 which indicates that the manufacture of the hexagonal molecular structure water is completed.

The detailed structure of a second embodiment of the present invention will now be explained.

Figure 6:
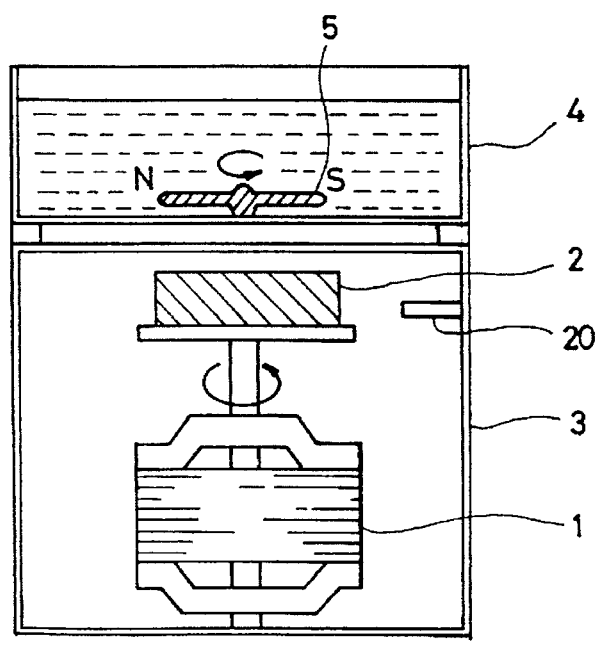
FIG. 6 is a schematic cross-sectional view showing a hexagonal molecular water structure manufacturing apparatus of a second embodiment according to the present invention.

Referring to FIG. 6, a hexagonal molecular structure water manufacturing apparatus and a method thereof includes the same elements as in FIG. 2 except for a hall sensor 20 which replace a central support shaft 7 and the weight detection sensor 6 in the first embodiment according to the present invention.

Figure 7:
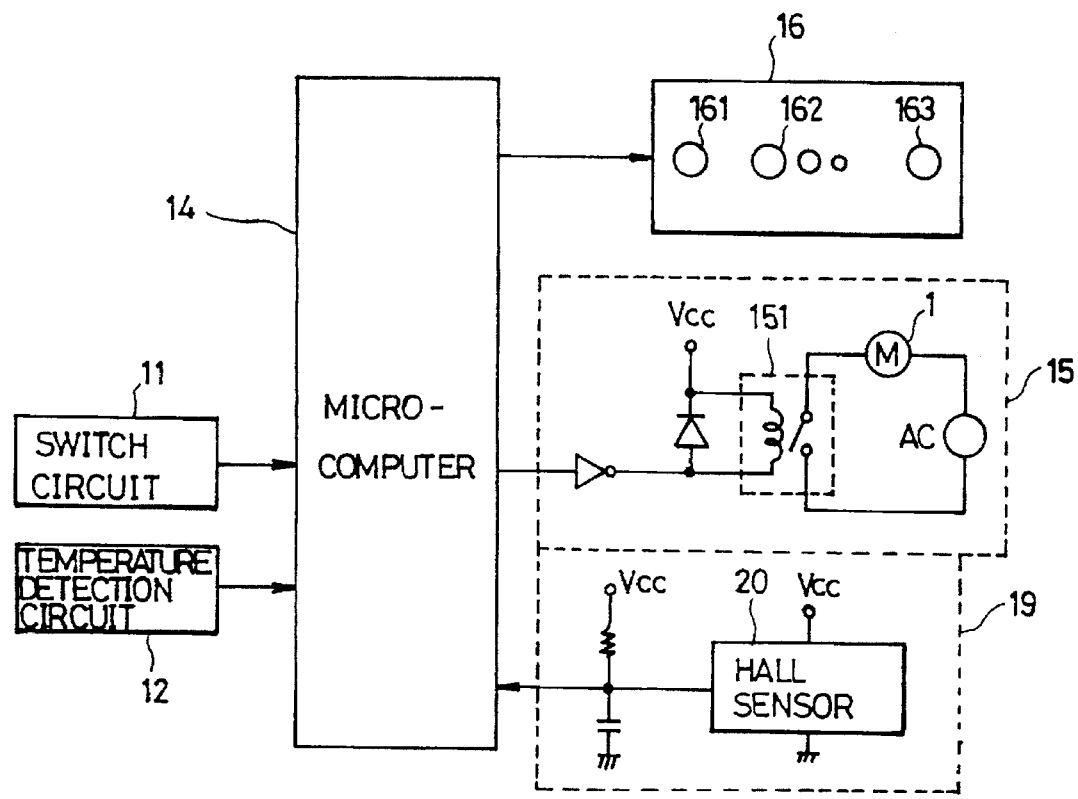
FIG. 7 is a block diagram showing a control circuit of the hexagonal molecular water structure manufacturing apparatus shown in FIG. 6.

Referring to FIG. 7, a hexagonal molecular structure water manufacturing apparatus and a method thereof includes the same elements as in FIG. 3 except for a weight detection circuit 19, which replace the weight detection circuit 13, for outputting a shaped waveform corresponding to the number of rotations of the motor 1, which is detected to count the weight of water.

Figure 8:
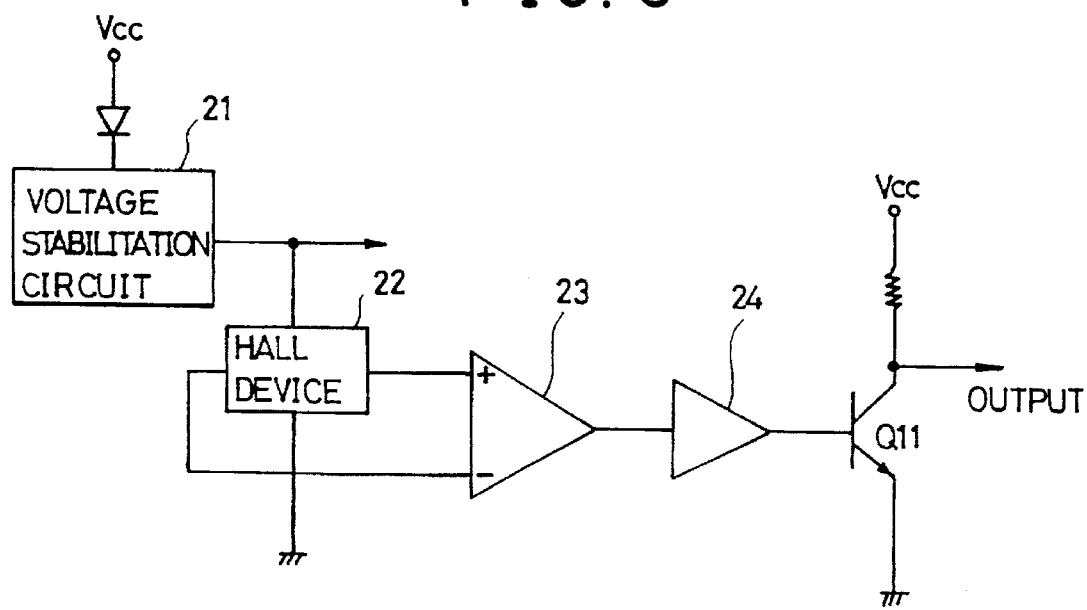
FIG. 8 is a detailed block diagram showing a hall sensor circuit shown in FIG. 7.

Here, referring to FIG. 8, the hall sensor 20 includes a voltage stabilization circuit 21 for outputting stabilized driving voltage VCC, a hall device 22 for detecting the number of rotations of the magnet 2 by receiving the driving voltage from the voltage stabilization circuit 21 and for outputting a pulse having a predetermined frequency in accordance with the detected number of rotations, an amplifier 23 for amplifying the output voltage of the hall device to a predetermined level, a hysteresis amplifier 24 for converting the output signals of the amplifier 23 into digital signals, and a transistor Q11 for outputting an external driving voltage in accordance with an output signal of the hysteresis amplifier 24.

Figure 10:
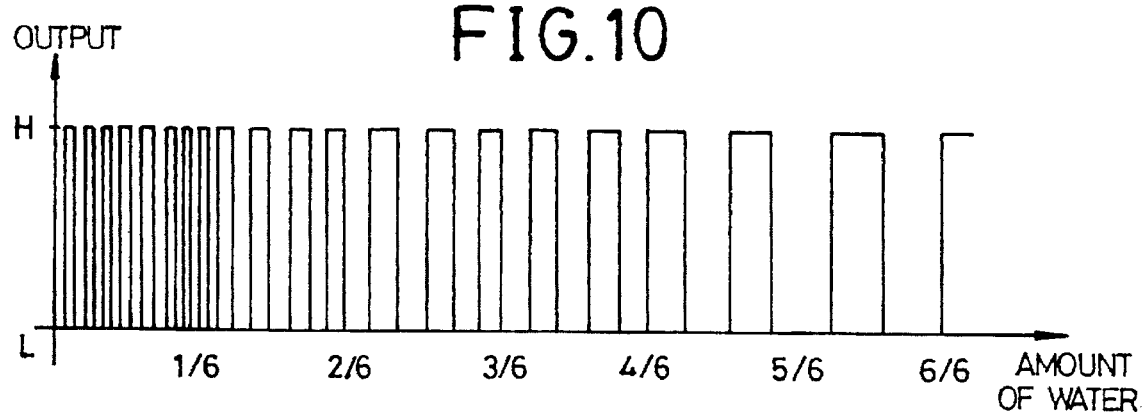
FIG. 10 is a graph showing an output waveform of the hall sensor in accordance with amount of water shown in FIG. 8.
Figure 11:
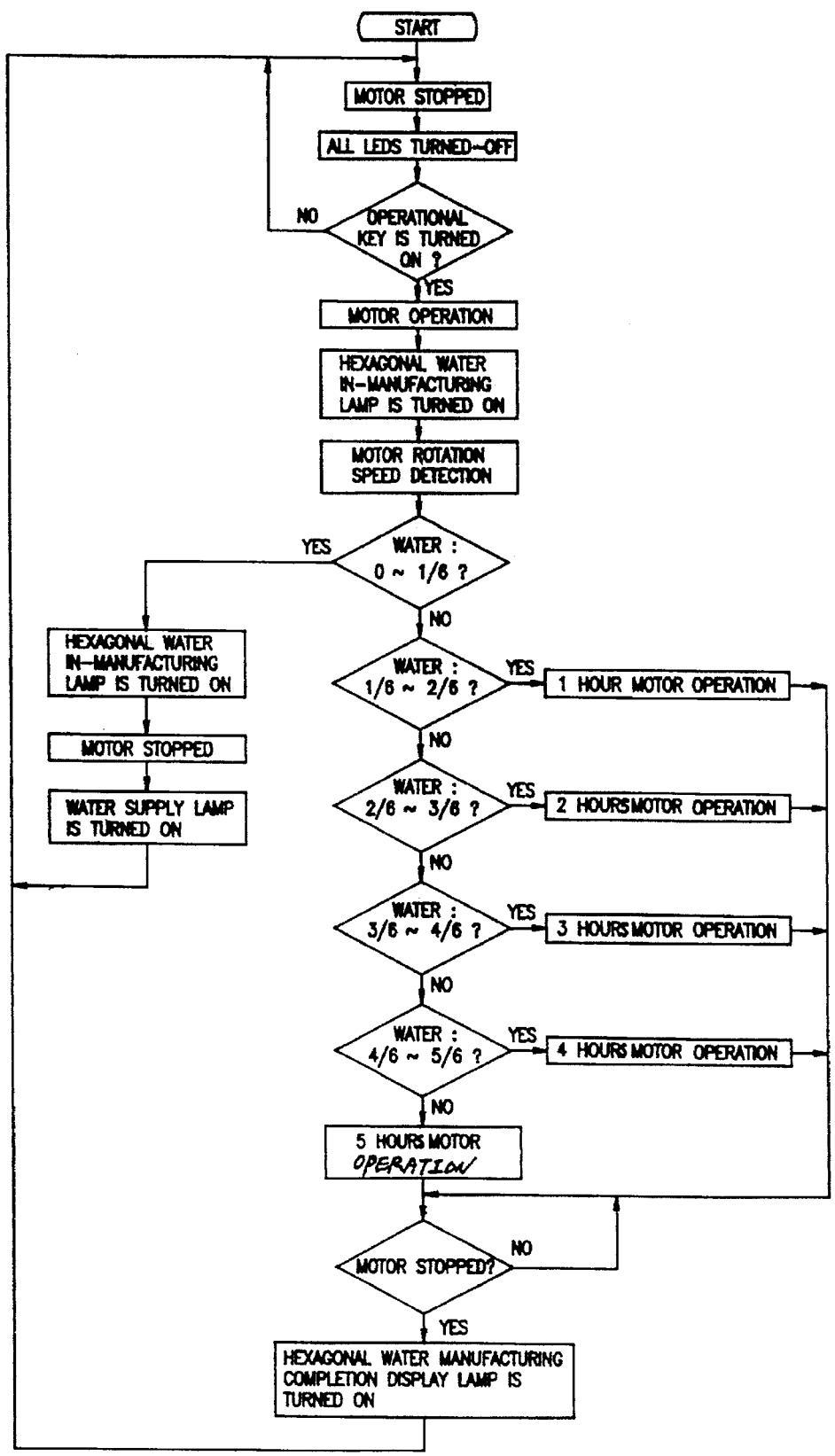
FIG. 11 is a flow chart showing a hexagonal molecular structure water manufacturing method shown in FIG. 7.

The detailed operation and effects thereof will now be explained with reference to FIGS. 9 to 11.

To begin with, in the state that the motor 1 is stopped, the microcomputer 14 controls the following lamps to be turned off: the water supply indicating lamp 161, the lamp 162 which indicates that the hexagonal molecular structure water is being manufactured, and the lamp 163 which indicates that the manufacture of the hexagonal molecular structure water is finished, respectively.

In this state, when a user fills the container 4 with water and turns on the operating key of the switch circuit 11 for beginning the manufacturing of hexagonal molecular structure water, the microcomputer 14 detects the turned-on state of the operating key and drives the motor 1 by turning on the relay 151 of the motor driving circuit 15 and then turns on the lamp 161, respectively.

Thereafter, the magnet 2 rotates as the motor 1 rotates, as a result that the magnet 5 also rotates by the magnetic force generated by the magnet 2.

Figure 9:
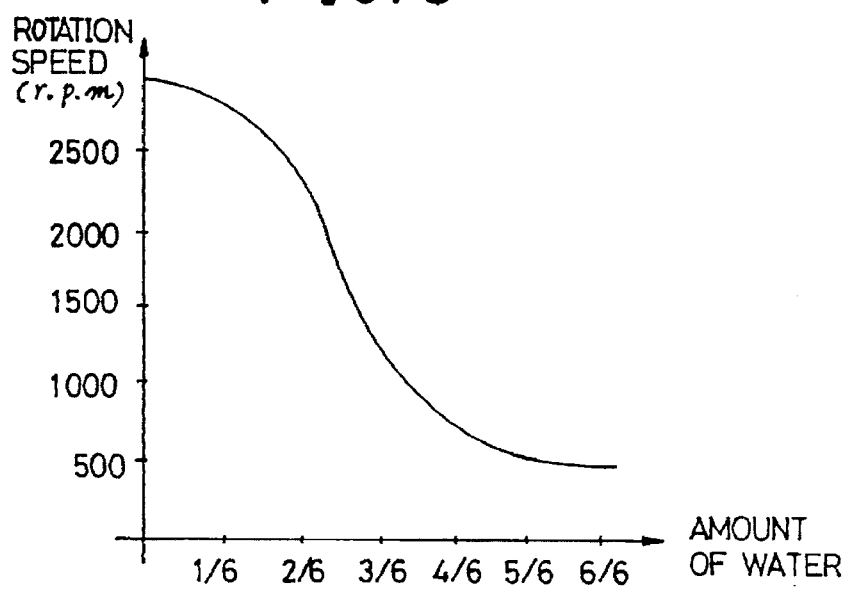
FIG. 9 is a graph showing a relationship between the amount of water and the rotation speed of a motor shown in FIG. 6.

At this time, referring to FIG. 9, as the amount of the water in the container 4 increases, the load applied to the motor 1 increases, so that the rotation speed of the motor 1 is reduced. Here, the rotation speed of the motor 1 is detected by the hall sensor circuit 20.

That is, as the magnetic force of the magnet 2 is applied to the hall device 22 of the hall sensor circuit 20 and then the corresponding current is applied to the hall sensor 22, a hall voltage is generated in a vertical direction against the direction of the magnetic force and the current. However, while the magnet 2 rotates, the magnetic force of the magnet 2 is alternated and then the hall device 22 outputs a low level voltage in accordance with the decrease of the rotation speed of the motor 1 as the load of water increases.

In addition, the output signal of the hall device 22 is amplified to a predetermined level by the amplifier 23 and is shaped by the hysteresis amplifier 24 and then is applied to the base terminal of the transistor Q11. Thereafter, the transistor Q11 outputs the pulse having a predetermined frequency in accordance with the rotation speed of the motor corresponding to the amount of water.

Accordingly, the microcomputer 14 judges the amount of water in the container 4 based on the frequency of the pulse of the hall sensor circuit 20. Here, if a predetermined ratio for the maximum amount of water, i.e., is judged to be below 1/6, the microcomputer 14 turns off the lamp 162 which indicates that the hexagonal molecular structure water is being manufactured, and stops the operation of the motor 1 and then turns on the water supply indicating lamp 161.

However, if the predetermined ratio for the maximum amount of water is judged to be over 1/6, that is, if its ratio is within a range of 1/6~2/6, 2/6~3/6, 3/6~4/6, 4/6~5/6, and 5/6~6/6, the microcomputer 14 operates the motor 1 for 1, 2, 3, 4, 5, and 6 hours, respectively.

Thereafter, when the operation of the motor 1 is finished, the microcomputer 14 turns on the lamp 14 for indicating that the manufacture of the hexagonal molecular structure water is finished.

Figure 12:
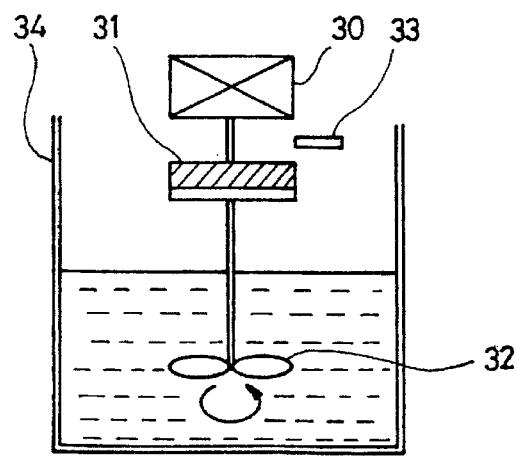
FIG. 12 is a schematic cross-sectional view showing a hexagonal molecular structure water manufacturing apparatus of a third embodiment of the present invention.

Meanwhile, referring to FIG. 12, there is shown a schematic cross-sectional view showing a hexagonal molecular structure water manufacturing apparatus of a third embodiment of the present invention. As shown therein, at the intermediate location of the motor 30 disposed at a predetermined portion of the main body(not shown) of the refrigerator is disposed a magnet 31. An alternating fan 32 is substantially immersed in water in a container 34. In addition, a hall sensor 33 is disposed at a predetermined portion of a magnet 31 for sensing the rotation speed of the fan 32.

The brief operation of the another embodiment according to the present invention will now be explained with reference to FIG. 12.

As the motor 30 rotates, the magnet 31 rotates and then the fan 32 also rotates in water in the container 34. At this time, the hall sensor 33 detects the rotation speed of the fan 32 to have a different rotation speed depending on the load, that is, amount of water.

The present invention is directed to detect the temperature and the weight of water in the container and then to control the alternating motor for a predetermined time in accordance with the detected temperature and weight, so that the hexagonal molecular structure water is advantageously manufactured.

In addition, the present invention is also directed to detect the rotation speed of the magnet coupled to the alternating motor using a hall sensor and then makes a predetermined water stream in accordance with the detected rotation speed of the motor corresponding to a predetermined load of the alternating water. At this time, even though, the hall sensor is used for long time, any possible variations of the sensor is sufficiently prevented because the sensor is not affected from the weight of water.

What is claimed is:

1. A hexagonal molecular structure water manufacturing apparatus comprising:

a container for storing water;

a first magnet for rotation in said container for producing upon rotation a hexagonal molecular structure for said water in said container and a second magnet connected to be driven by a motor and magnetically coupled to said first magnet to drive said first magnet;

a weight detection section including a weight detection sensor for detecting a weight of the water in the container and for generating a weight signal corresponding to said detected weight;

a temperature sensing circuit for providing a temperature signal representing the temperature of said water;

a switch circuit for providing a starting signal;

a microcomputer including first means for determining whether or not said temperature signal lies within a predetermined range upon the presence of said starting signal, second means responsive to said first means for determining a time period for rotation of said motor dependent upon the weight of the water in said container when said temperature signal lies within said predetermined range and if the weight of the water in said container is above a predetermined value, and fourth means responsive to said third means for generating a first control signal for a length of time equal to said time period; and a motor driving section for driving said motor to rotate said first and second magnets in accordance with said first control signal from the forth means of said microcomputer.

2. The apparatus of claim 1, wherein said weight detection section comprises a capacitor which includes a first electrode and a second electrode disposed in parallel for generating an oscillating signal in correspondence to a distance between said electrodes that varies as a function of the weight of water in the container, and a counter for counting said oscillating signal to produce said weight signal.

3. The apparatus of claim 1, wherein said weight detection section includes a hall sensor, said hall sensor comprising:

a voltage stabilizer for out-putting a stabilized driving voltage;

a hall effect device for detecting a number of rotations of the second magnet connected to the motor in accordance with said stabilized driving voltage, and for outputting a pulse signal having a frequency corresponding to said detected number of rotations;

an amplifier for amplifying said pulse signal from said hall effect device;

a hysteresis amplifier for converting a signal from said amplifier into a digital signal; and a transistor for out-putting an external driving voltage corresponding to said weight signal in accordance with said digital signal from said hysteresis amplifier.

4. The apparatus according to claim 1, wherein said control means includes fifth means for generating a second control signal when the weight of said water is below said predetermined value, sixth means for generating a third control signal when said motor is being activated to indicate that water having said hexagonal molecular structure is being produced, and seventh means for generating a fourth control signal when said time period has lapsed to indicate that the manufacture of the water having said hexagonal molecular structure has been completed.

5. The apparatus according to claim 1, further comprising a display section including a first display means responsive to said second control signal for indicating when the weight of the water in said container is below a predetermined value, second display means responsive to said third control signal for indicating when said motor is activated and the water having said hexagonal molecular structure is being produced, and a third display means responsive to said fourth control signal for indicating when said time period has lapsed and that the manufacture of the water having said hexagonal molecular structure has been completed.

* * * * *